US012740749B2

(12) United States Patent
Sette

(10) Patent No.: US 12,740,749 B2
(45) Date of Patent: Sep. 22, 2026

(54) ARRANGEMENT WITH CATHETER AND SENSOR ARRANGEMENT

(71) Applicant: MEDYRIA AG, Winterthur (CH)

(72) Inventor: Mauro Massimo Sette, Winterthur (CH)

(73) Assignee: MEDYRIA AG, Winterthur (CH)

( * ) Notice: Subject to any disclaimer, the term of this patent is extended or adjusted under 35 U.S.C. 154(b) by 479 days.

(21) Appl. No.: 16/966,877

(22) PCT Filed: Feb. 5, 2019

(86) PCT No.: PCT/EP2019/052731
§ 371 (c)(1),
(2) Date: Jul. 31, 2020

(87) PCT Pub. No.: WO2019/149954
PCT Pub. Date: Aug. 8, 2019

(65) Prior Publication Data

US 2021/0038157 A1 Feb. 11, 2021

(30) Foreign Application Priority Data

Feb. 5, 2018 (DE) ..................... 10 2018 102 538.6

(51) Int. Cl.
*A61B 5/00* (2006.01)
*A61B 5/026* (2006.01)
*A61B 5/06* (2006.01)

(52) U.S. Cl.
CPC ............ *A61B 5/6852* (2013.01); *A61B 5/026* (2013.01); *A61B 5/065* (2013.01);
(Continued)

(58) Field of Classification Search
CPC ....... A61B 5/6852–6859; A61B 5/6848–6851; A61B 5/026; A61B 5/065;
(Continued)

(56) References Cited

U.S. PATENT DOCUMENTS 4,947,688 A * 8/1990 Yagawara ................. G01P 5/10
73/204.26
5,921,923 A * 7/1999 Kuck ................. A61B 18/1492
607/122
(Continued)

FOREIGN PATENT DOCUMENTS

CN 105828709 A 8/2016
CN 105848573 A 8/2016
(Continued)

OTHER PUBLICATIONS

B. De Bruyne, J. Bartunk, S.U. Sys, N. H. J. Pijl, G. R. Heyndrickx, and W. Wijns, "Simultaneous coronary pressure and flow velocity measurements in humans: Feasibility, reproducibility, and hemodynamic dependence of coronary flow velocity reserve, hyperemic flow versus pressure slope index, and fractional flow reserve," Circulation, vol. 94, No. 8, pp. 1842-1849, 1996.
(Continued)

*Primary Examiner* — Jacqueline Cheng
*Assistant Examiner* — Samuel C Kim
(74) *Attorney, Agent, or Firm* — MOSER TABOADA

(57) ABSTRACT

An arrangement for providing information of an alignment of a catheter is provided. The arrangement comprises a catheter (140). The arrangement comprises a sensor arrangement. The sensor arrangement comprises a first sensor (101) and a second sensor (102). The first and the second sensors are adapted to measure respective velocities of the fluid flow. The first and second sensors are arranged at a circumference of the catheter. The first and second sensors provide information such that an alignment of the catheter with respect to a direction of the fluid flow is determinable based on the respective velocities of the fluid flow measured by the first and second sensors.

12 Claims, 13 Drawing Sheets

Figure 1:
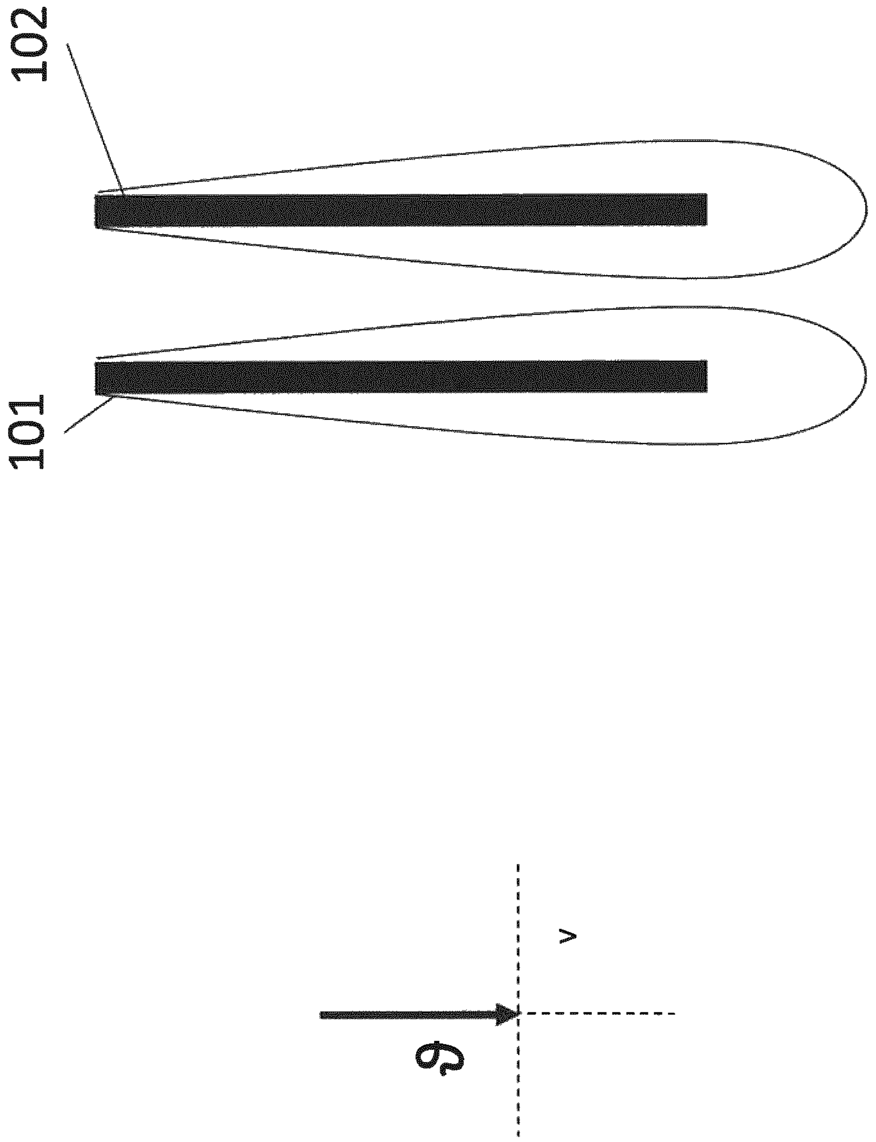

(52) U.S. Cl.
CPC ................. *A61B 2562/0247* (2013.01); *A61B 2562/0271* (2013.01); *A61B 2562/043* (2013.01); *A61B 2562/227* (2013.01)

(58) Field of Classification Search
CPC .... A61B 2562/0247; A61B 2562/0271; A61B 2562/043
See application file for complete search history.

(56) References Cited

U.S. PATENT DOCUMENTS

| | | | | |
|---|---|---|---|---|
| 9,717,422 | B2 * | 8/2017 | Flanders | A61B 1/04 |
| 2005/0033136 | A1 * | 2/2005 | Govari | A61B 5/287 606/41 |
| 2007/0078352 | A1 | 4/2007 | Pijls | |
| 2010/0004531 | A1 * | 1/2010 | Passmore | A61B 5/028 600/425 |
| 2012/0071783 | A1 | 3/2012 | Klee et al. | |
| 2014/0249520 | A1 * | 9/2014 | Ghaffari | A61B 34/35 606/34 |
| 2015/0342672 | A1 * | 12/2015 | Bencini | A61B 8/12 606/41 |
| 2016/0015323 | A1 * | 1/2016 | Tathireddy | A61B 5/4842 600/585 |
| 2016/0113628 | A1 | 4/2016 | Sette | |
| 2016/0228061 | A1 | 8/2016 | Kallback et al. | |
| 2019/0033109 | A1 * | 1/2019 | Lee | A01G 7/00 |
| 2019/0175056 | A1 * | 6/2019 | Berkowitz | A61M 25/0009 |

FOREIGN PATENT DOCUMENTS

| | | | | |
|---|---|---|---|---|
| CN | 106132310 | A | 11/2016 | |
| GB | 2361537 | A | 10/2001 | |
| WO | WO-9421170 | A1 * | 9/1994 | A61B 5/0422 |
| WO | WO 2004007014 | A1 | 1/2004 | |
| WO | WO-2014025255 | A1 * | 2/2014 | A61B 5/02007 |
| WO | WO-2014/100110 | A2 | 6/2014 | |
| WO | WO-2014200436 | A1 * | 12/2014 | A61B 5/0008 |
| WO | WO-2016/038496 | A1 | 3/2016 | |
| WO | WO-2017/134206 | A1 | 8/2017 | |

OTHER PUBLICATIONS

M. Siebes, B. J. Verhoeff, M. Meuwissen, R.J. De Winter, J.A. E. Spaan, and J.J. Piek, “Single-Wire Pressure and Flow Velocity Measurement to Quantify Coronary Stenosis Hemodynamics and Effects of Percutaneous Interventions,” Circulation, vol. 109, No. 6, pp. 756-762, 2004.

“Bernoulli’s equation” (Wikipedia).

* cited by examiner

ARRANGEMENT WITH CATHETER AND SENSOR ARRANGEMENT

Examples relate to concepts for providing information of an alignment of a catheter and applications thereof and in particular to an arrangement for providing information of an alignment of a catheter.

There is a class of surgical procedures called interventional procedures or minimal invasive procedures, which foresees the introduction of a catheter within the human vasculature to measure quantities like pressure and blood flow velocity. In a common procedure the catheter is introduced from an opening in a blood vessel, e.g. in the groin or in the brachial artery. Through this opening the catheter is then advanced until the region of interest, often a coronary branch and the intervention is performed there.

Two commonly measured quantities are pressure and blood flow velocity, which are processed to calculate the two indexes called fractional flow reserve (FFR), and coronary flow velocity reserve (CFVR).

Both pressure-derived myocardial fractional flow reserve (FFR) and coronary flow velocity reserve (CFVR) have been evaluated as predictors of inducible ischemia, as measured by non-invasive stress tests, and indicate adverse events after stent placement.

The combination of pressure and flow velocity into an index of hyperemic stenosis resistance significantly improves diagnostic accuracy as assessed by noninvasive ischemic testing, especially in cases with discordant outcomes between traditional parameters.

The relationship between distal coronary velocity and trans-stenotic pressure gradient is almost entirely determined by the coronary stenosis and is thus by definition well suited to evaluate its hemodynamic severity.

In all the vascular procedures, such as stenting and ballooning of stenosis e.g. coronary or peripheral procedures, the flow velocity measurement and pressure measurements can always be used as diagnostic tool or for monitoring success of procedures.

A commonly used technology for measuring the blood flow velocity and relative derived indexes is use of ultrasound. The catheters are equipped with a piezoelectric crystal that, when excited, can emit ultrasound. The ultrasound is then reflected by the natural blood scatters and the measurements of the Doppler frequency shift or the time of flight are used to derive the fluid's velocity.

At the same time the catheter can be equipped with an additional pressure sensor which may describe an energetic status of the fluid section according to Bernoulli's equation:

$$\frac{v^2}{2} + gz + \frac{p}{\rho} = \text{constant}$$

where:

v=fluid's velocity, measured with the ultrasonic sensor p=pressure, measured with pressure sensor g=gravity acceleration (constant)

z=piezometric height (can be assumed constant)

ρ=blood's volumetric mass (constant)

For example, in order to describe the fluid flow into a vessel, both pressure and flow velocity may be necessary. An accurate knowledge of both pressure and flow velocity leads to a complete characterization of the fluid flow and to a definition of important diagnostic quantities such as the peripheral vessel's impedance.

For example, combining blood flow velocity and pressure measurement may be used on a guidewire for assessing a level of a stenosis.

The measurement made with an ultrasound/doppler sensor may be subject to the angle of incidence of the ultrasonic wave with the direction of the blood flow velocity according to the formula:

$$f_d = -\frac{2 f_s v}{c}\cos\theta$$

where:

$f_d$=frequency shift $f_s$=frequency of the source v=fluid's velocity c=velocity of sound cosθ=angle between direction of the velocity and direction of the emitted sound Consequently, the measurement is strongly dependent on the angle θ which cannot be controlled in an endovascular procedure, i.e. the angle θ depending on the catheter position can range from 0° to 90° giving completely different measurements.

A problem may be a repeated injection of intracoronary adenosine, because a signal of an instantaneous blood flow velocity cannot be measured with enough sufficient accuracy to rely on a mean blood flow velocity.

Arrangements may have to be optimized with respect to positioning of sensors on catheters. Nevertheless, it is desired to form an arrangement enabling better measuring accuracy.

There may be a demand to provide concepts for equipping catheters with sensor arrangements allowing a better measurement of blood flow velocity, giving direct information on a correct positioning of a catheter.

Such a demand may be satisfied by the subject-matter of the claims.

According to an aspect, an arrangement for providing information of an alignment of a catheter (in a blood vessel) is provided. The arrangement comprises a catheter or another elongated body, e.g. a wire or the like. The arrangement comprises a sensor arrangement. The sensor arrangement comprises a first sensor and a second sensor.

The first and the second sensors are adapted to measure respective velocities of the fluid flow. The first and second sensors are arranged at (not directly on) a circumference of the catheter or the other elongated body, e.g. the wire. The first and second sensors provide information such that an alignment of the catheter (or the other elongated body, e.g. the wire) with respect to a direction of the fluid flow is determinable based on the respective velocities of the fluid flow measured by the first and second sensors.

This may provide an advanced catheter arrangement for better alignment of the catheter during application of a catheter.

Although in the following it is mainly referred to a catheter, the principles described below are equally applicable to other elongated bodies such as wires or the like.

The first and second sensors may have a semi-circular shape.

The semi-circular shape may have a flat part and an arc. The flat parts of the first and second sensors may be parallel to each other.

The sensor arrangement may further comprise a third sensor. The third sensor may be adapted to measure a temperature of a fluid corresponding to the fluid flow.

The sensor arrangement may further comprise a fourth sensor. The fourth sensor may be a pressure sensor adapted to measure pressure of a fluid corresponding to the fluid flow.

The first and second sensors may be spaced from the catheter. For example, the first is and second sensors do not touch the catheter.

The first sensor may be distant from the second sensor by a gap. The first sensor may comprise a first dimension of the first sensor. The first sensor may comprise a second dimension of the first sensor. The first sensor may comprise a third dimension of the first sensor. The first dimension of the first sensor may be larger than the second dimension of the first sensor. The second dimension of the first sensor may be larger than the third dimension of the first sensor. The first dimension of the first sensor may be a length of the first sensor. The second dimension of the first sensor may be width of the first sensor. The third dimension may be a height of the first sensor.

The second sensor may comprise a first dimension of the second sensor. The second sensor may comprise a second dimension of the second sensor. The second sensor may comprise a third dimension of the second sensor. The first dimension of the second sensor may be larger than the second dimension of the second sensor. The second dimension of the second sensor may be larger than the third dimension of the second sensor. The first dimension of the second sensor may be a length of the second sensor. The second dimension of the second sensor may be width of the second sensor. The third dimension may be a height of the second sensor.

An area of one of the two sensors and an area of the other one of the two sensors may not be in a same plane (according to a geometry of the catheter). The two sensors may be displaced at least a width of one of the two sensors. The two sensors may be displaced by less than a diameter of the catheter.

The first dimension of the first sensor may be parallel to the first dimension of the second sensor. The first dimension of the first sensor may be aligned with the first dimension of the second sensor.

For example, the second dimension of the first sensor is not parallel to the second dimension of the second sensor. For example, the second dimension of the first sensor is not aligned with the second dimension of the second sensor.

For example, the third dimension of the first sensor is not parallel to the third dimension of the second sensor. For example, the third dimension of the first sensor is not aligned with the third dimension of the second sensor.

The first sensor may have a semi-circular shape. The second sensor may have a semi-circular shape. The first and second sensor may be in the form of a semi-circle. A flat part of the semi-circle of the first sensor and a flat part of the semi-circle of the second sensor may be parallel.

The semi-circular shape may have the advantage that the sum of the two signals coming from the sensors is always proportional to a blood flow velocity magnitude. Further, the sum of the two signals may be insensitive to the orientation. However, information about the orientation may be derivable by analysing the difference between the two signals measured by the respective first and second sensors.

The sensor arrangement may further comprise a third sensor. The third sensor may be a pressure sensor. The pressure sensor may be adapted to measure a current pressure of the fluid flow. The pressure sensor may also be in a separate plane compared to the first and second sensors. The pressure sensor can be a semiconductor, capacitive, piezoresistive based and/or optical fiber pressure sensor.

The first, second and third dimensions may be aligned in parallel.

The arrangement may further comprise a flexible carrier. The flexible carrier may include (integrate/embed) the sensor arrangement. The carrier may be arranged (wrapped around) along the circumference of the catheter.

The sensor arrangement may be spaced from the catheter by at least half a height of the flexible carrier. The sensor arrangement may be distant/spaced from the catheter by less than a height of the flexible carrier. The flexible carrier may be a foil, for example a polyimide foil. For example, the first and second sensors are screen printed on the foil. The carrier may be glued to the catheter.

A width of the carrier may be smaller than the circumference of the catheter. The width of the carrier may be larger than a diameter of the catheter. A length of the carrier may be aligned with a length of the catheter.

The flexible carrier may further include electrical contact pads. The electrical contact pads may be arranged and adapted to enable an electrical connection to the first and second sensors. Further, the electrical contact pads may be arranged on/at/in the flexible carrier to enable an electrical connection to the third sensor. For example, a first plurality of the electrical contact pads are arranged on/at/in the flexible carrier and adapted to enable an electrical connection to the first sensor. For example, a second plurality of the electrical contact pads are arranged on/at/in the flexible carrier and adapted to enable an electrical connection to the second sensor. For example, a third plurality of the electrical contact pads are arranged on/at/in the flexible carrier and adapted to enable an electrical connection to the second sensor.

The electrical contact pads can consist of the first, second and third plurality of the contact pads.

The arrangement may further comprise a processing unit. The processing unit may be adapted to process the respective velocities of the fluid flow provided by the first and second sensors. The processing unit may be adapted to provide information for aligning the catheter in the fluid flow based on the processing.

The first and second sensors may be provided/arranged at opposite sides of the catheter and parallel to each other.

For example, areas of the first and second sensors may be on parallel planes.

The first and second sensors may be arranged at the circumference of the catheter. The first and second sensors may be spaced to each other. The spacing may be between 10 μm and 15% of the circumference.

The first and second sensors may be thermal (blood) flow velocity sensors.

The processing unit may be electrically connectable or connected to the electrical contact pads. The electrical connection may be established by bonding electrical wires connected to the processing unit to the electrical contact pads.

The processing unit may be electrically connected to the electrical contact pads (via wires). The sensor arrangement may be connectable or connected to the processing unit via the electrical contact pads. The first and second sensors may be adapted to provide the respective velocities to the processing unit. The processing unit may be adapted to provide information about whether the two sensors are in alignment with the fluid flow.

A distance between the first and second sensors may be larger than a quarter of the circumference of the catheter. The distance between the first and second sensors may be smaller than a half of the circumference of the catheter. The distance between the first and second sensors may be larger than a quarter (or a half) of a diameter of the catheter. The distance between the first and sensors may be smaller than the diameter of the catheter.

The sensor arrangement may further comprise a fourth sensor. The fourth sensor may be a temperature sensor. The temperature sensor may be adapted to measure the temperature of the fluid. The temperature sensor may also be in a separate plane compared to the first and second sensors. The temperature sensor may have a first dimension. The temperature sensor may have a second dimension. The temperature sensor may have a third dimension. The first dimension may be a length. The second dimension may be a width. The third dimension may be a height. The first dimension may be larger than the second dimension. The second dimension may be larger than the third dimension. The first dimension of the pressure sensor may be substantially equal to the first dimension of the first/second sensor. The second dimension of the pressure sensor may be substantially equal to the second dimension of the first/second sensor. The third dimension of the temperature sensor may be substantially equal to the third dimension of the first/second sensor. Thus, the dimension of the first, second and third sensors may be substantially the same.

The temperature sensor may be adapted to perform a temperature measurement. The temperature measurement may be used to compensate the measurement drift caused by the sensor water absorption or temperature fluctuation of the fluid.

Additionally the temperature can be used as detector, to identify when the catheter (or elongated body) is for example inserted into a patient's body. After detection, the measurement may be started. Further, the temperature sensor may be adapted to trigger a signal and enabling the processing unit to start processing of the first and second sensors' provided information.

A distance between the fourth sensor and the first/second sensor may be smaller than the circumference (or a half or a quarter of the circumference) of the catheter. The distance between the third sensor and the first/second sensor may be larger than the 1 (or 2 or 3 or 4) times the width of the first or second sensor.

The first, second and third sensors may be aligned on an area of the carrier. The carrier is flat and the first, second and third sensors are arranged in a plane, when the carrier is not bend or wrapped around the catheter (first condition).

Measuring results of the first and second sensors may be the same when the catheter is aligned with the fluid flow. Measuring results of the first and second sensors may not be the same, when the catheter is not aligned with the fluid flow. Thus, the alignment of the first and second sensors with the fluid flow may mirror/reflect the alignment of catheter with the fluid flow.

For example, in a first condition, when the carrier is not wrapped around the catheter, areas of the first and second (and third) sensors are in a same plane. For example, in a second condition, when the carrier is wrapped around the catheter, the areas of the first and second (and third) sensors are not in the same plane.

The arrangement may further comprise an outputting unit. The outputting unit may be connected to the processing unit. The outputting unit may be adapted to indicate an alignment of the catheter to be moved within the fluid flow. The indication may be based on the processed information.

It is clear to a person skilled in the art that the statements set forth herein under use of hardware circuits, software means, or a combination thereof may be implemented. The software means can be related to programmed microprocessors or a general computer, an ASIC (Application Specific Integrated Circuit) and/or DSPs (Digital Signal Processors). For example, the processing unit and outputting unit may be implemented partially as a computer, a logical circuit, an FPGA (Field Programmable Gate Array), a processor (for example, a microprocessor, microcontroller (pC) or an array processor)/a core/a CPU (Central Processing Unit), an FPU (Floating Point Unit), NPU (Numeric Processing Unit), an ALU (Arithmetic Logical Unit), a Coprocessor (further microprocessor for supporting a main processor (CPU)), a GPGPU (General Purpose Computation on Graphics Processing Unit), a multi-core processor (for parallel computing, such as simultaneously performing arithmetic operations on multiple main processor(s) and/or graphical processor(s)) or a DSP. It is further clear to the person skilled in the art that even if the herein-described details will be described in terms of a method, these details may also be implemented or realized in a suitable device, a computer processor or a memory connected to a processor, wherein the memory can be provided with one or more programs that perform the method, when executed by the processor. Therefore, methods like swapping and paging can be deployed.

It is also to be understood that the terms used herein are for purpose of describing individual embodiments and are not intended to be limiting. Unless otherwise defined, all technical and scientific terms used herein have the meaning which corresponds to the general understanding of the skilled person in the relevant technical field of the present disclosure; they are to be understood too neither too far nor too narrow. If technical terms are used incorrectly in the present disclosure, and thus do not reflect the technical concept of the present disclosure, these should be replaced by technical terms which convey a correct understanding to the skilled person in the relevant technical field of the present disclosure. The general terms used herein are to be construed based on the definition in the lexicon or the context. A too narrow interpretation should be avoided.

It is to be understood that terms such as e.g. "comprising" "including" or "having" etc. mean the presence of the described features, numbers, operations, acts, components, parts, or combinations thereof, and do not exclude the presence or possible addition of one or more further features, numbers, operations, acts, components, parts or their combinations.

Although terms like "first" or "second" etc. may be used to describe different components or features, these components or features are not to be limited to these terms. With the above terms, only one component is to be distinguished from the other. For example, a first component may be referred to as a second component without departing from the scope of the present disclosure; and a second component may also be referred to as a first component. The term "and/or" includes both combinations of the plurality of related features, as well as any feature of that plurality of the described plurality of features.

In the present case, if a component is "connected to", "in communication with" or "accesses" another component, this may mean that it is directly connected to or directly accesses the other component; however, it should be noted that another component may be therebetween. If, on the other hand, a component is "directly connected" to another component or "directly accesses" the other component, it is to be understood that no further components are present therebetween.

In the following, the preferred embodiments of the present disclosure will be described with reference to the accompanying drawings; the same components are always provided with the same reference symbols.

In the description of the present disclosure, detailed explanations of known connected functions or constructions are omitted, insofar as they are unnecessarily distracting from the present disclosure; such functions and constructions are, however, understandable to the skilled person in the technical field of the present disclosure. The accompanying drawings are illustrative of the present disclosure and are not to be construed as a limitation. The technical idea of the present disclosure is to be construed as comprising, in addition to the accompanying drawings, all such modifications, variations and variants.

Other objects, features, advantages and applications will become apparent from the following description of non-limiting embodiments regarding the accompanying drawings. In the drawings, all described and/or illustrated features, alone or in any combination form the subject matter disclosed therein, irrespective of their grouping in the claims or their relations/references. The dimensions and proportions of components or parts shown in the figures are not necessarily to scale; these dimensions and proportions may differ from illustrations in the figures and implemented embodiments.

Figure 2:
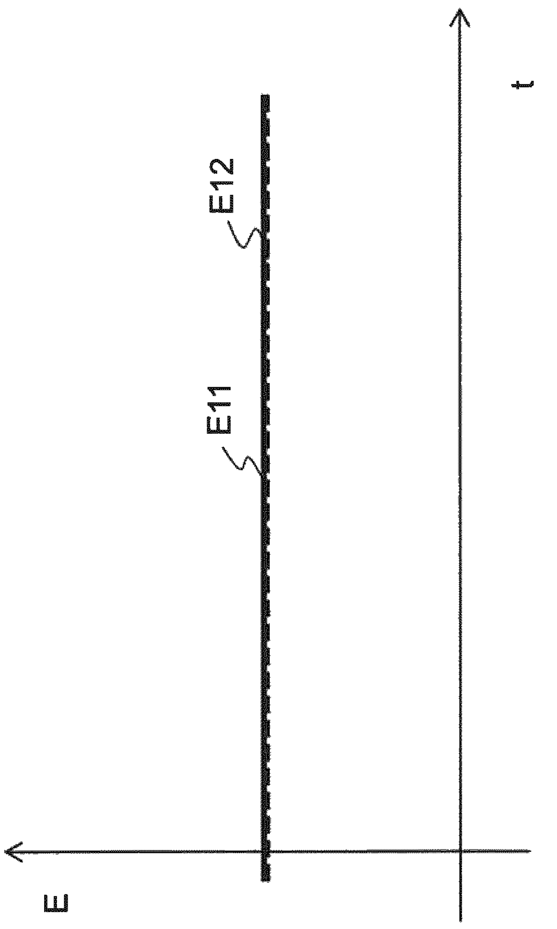
Figure 3:
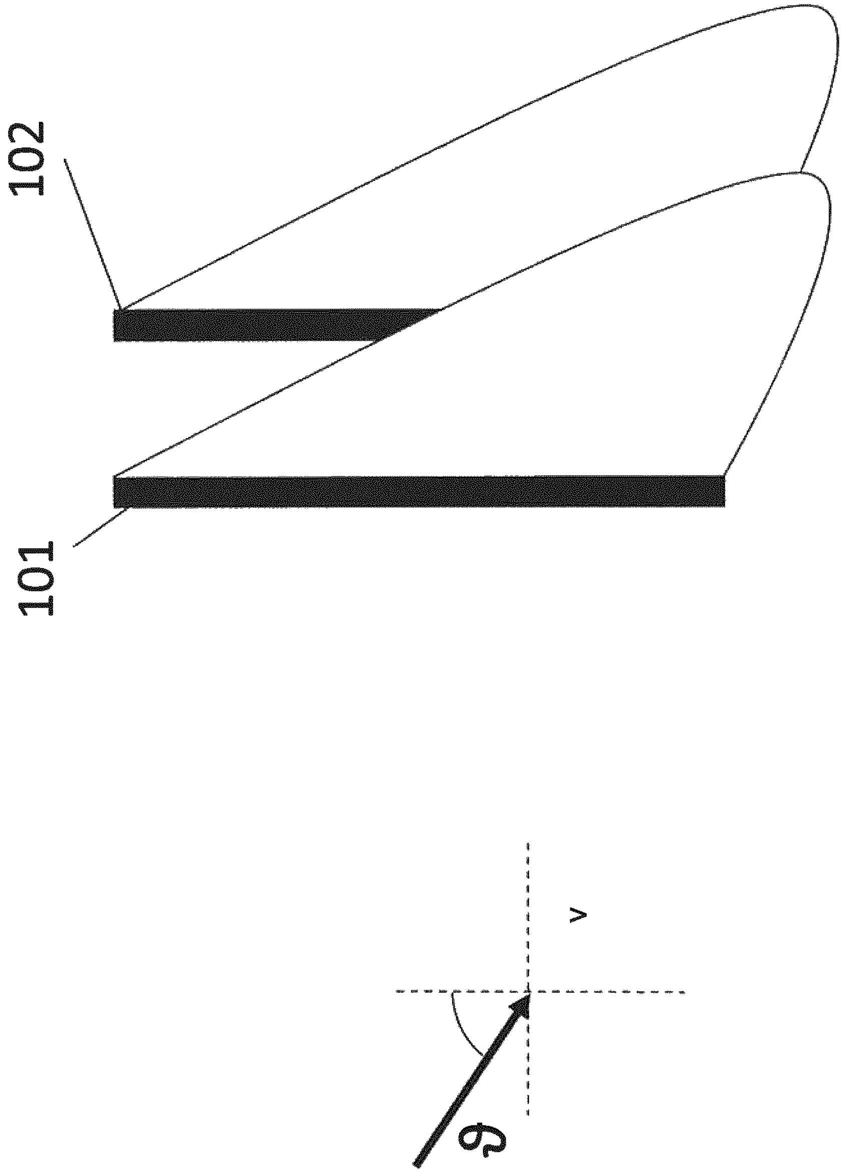
Figure 4:
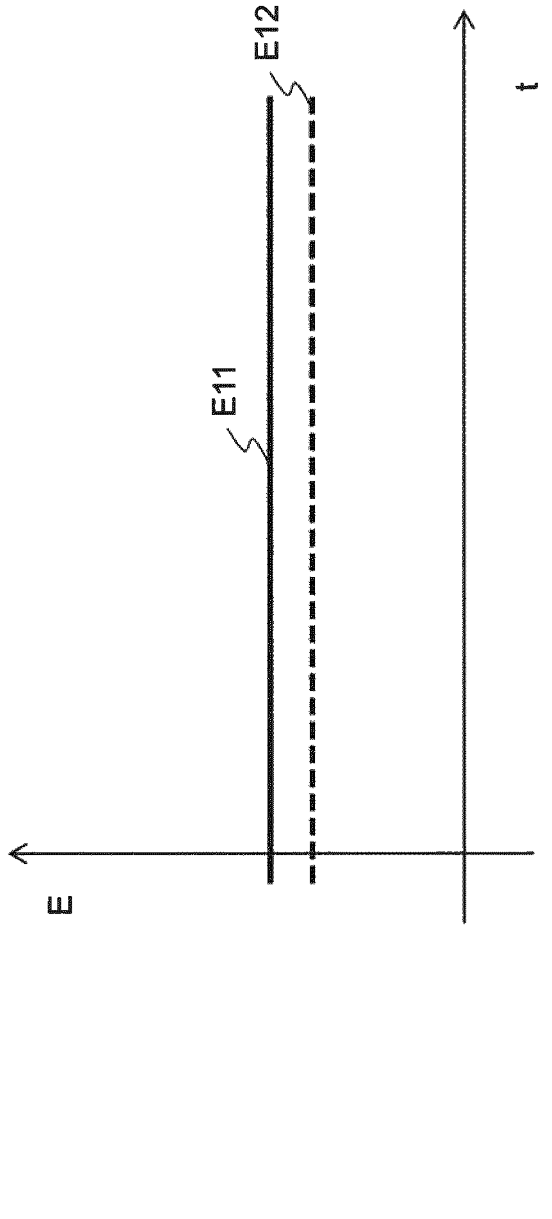
Figure 5:
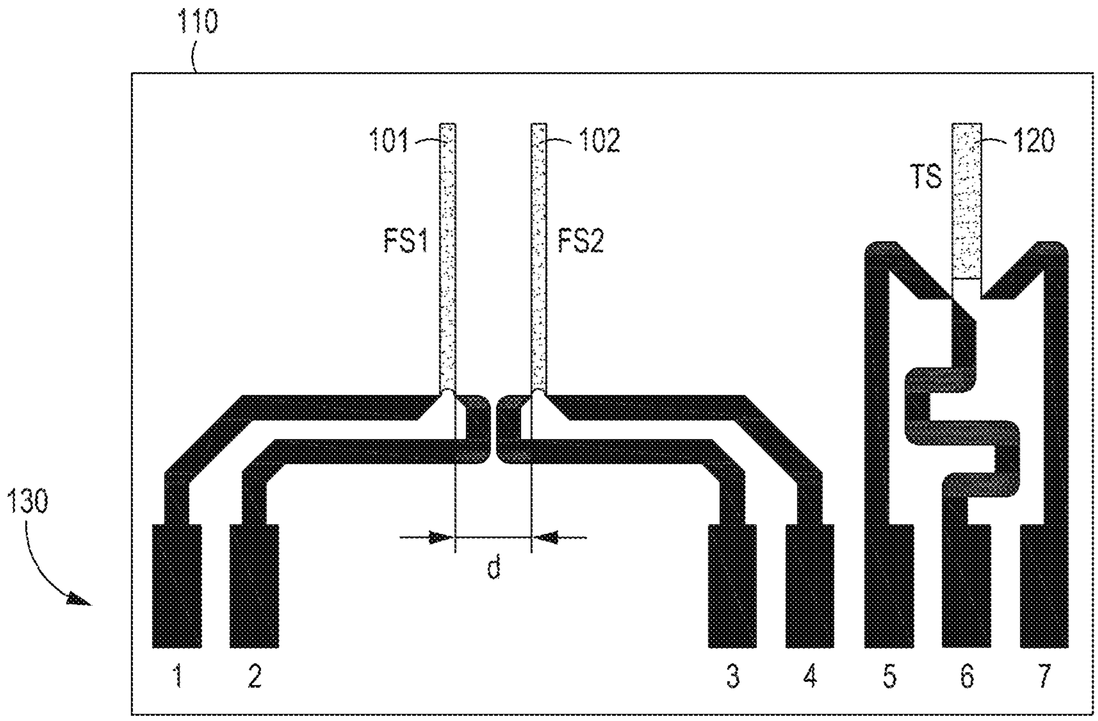
Figure 6:
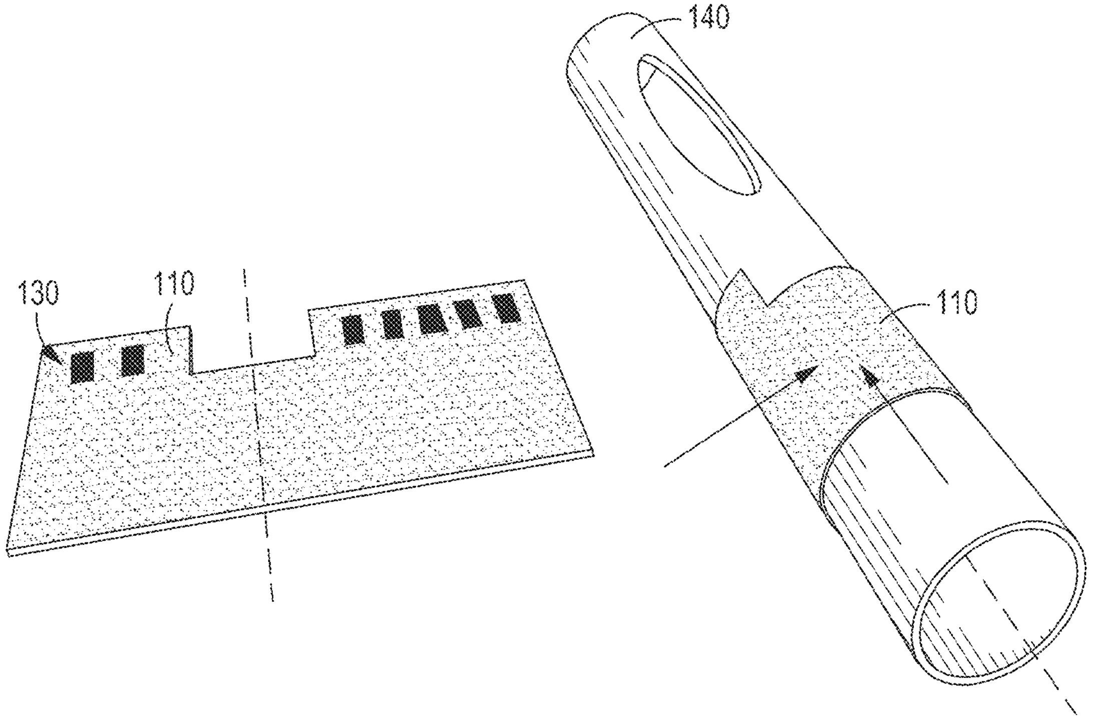
Figure 7:
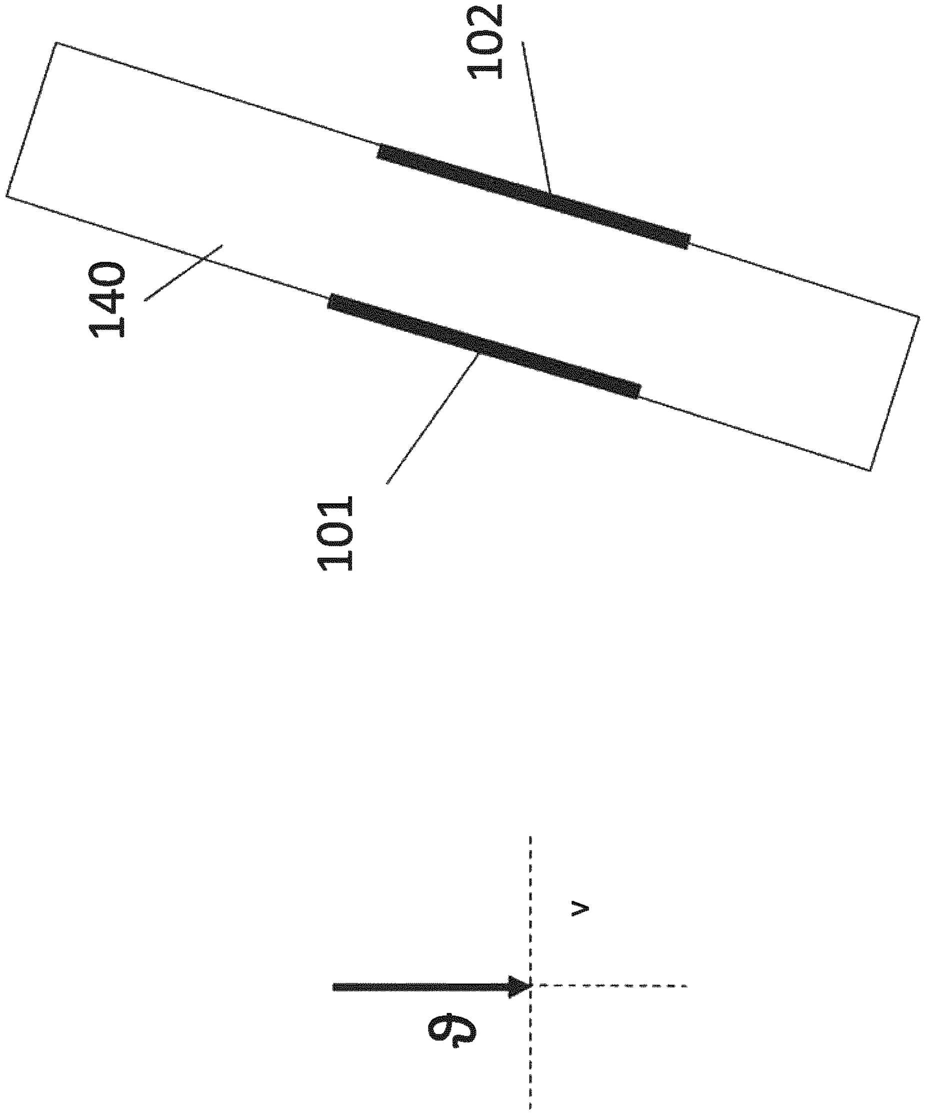
Figure 8:
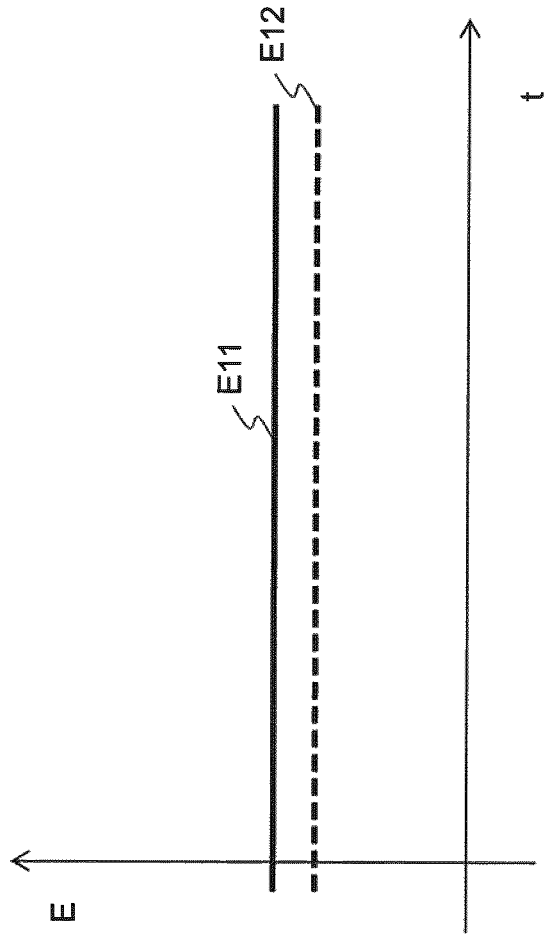
Figure 9:
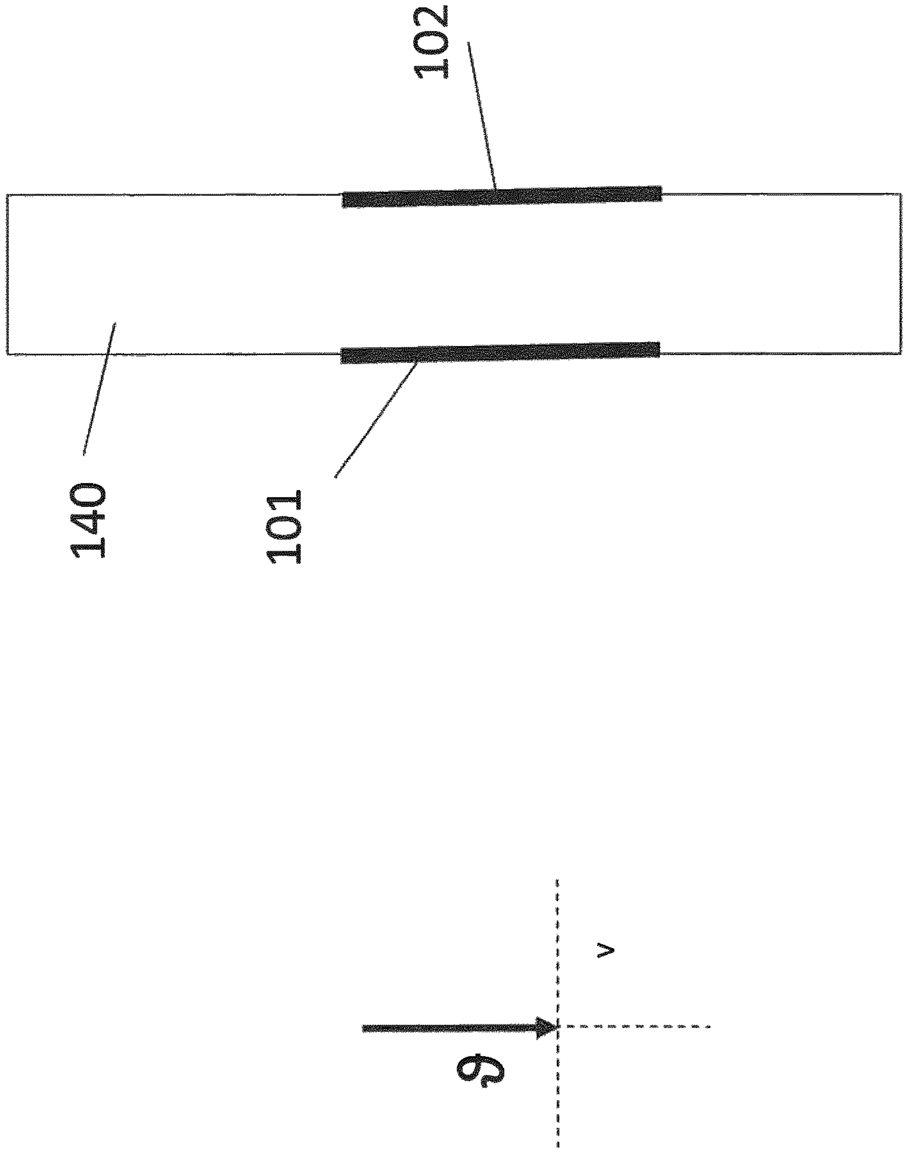
Figure 10:
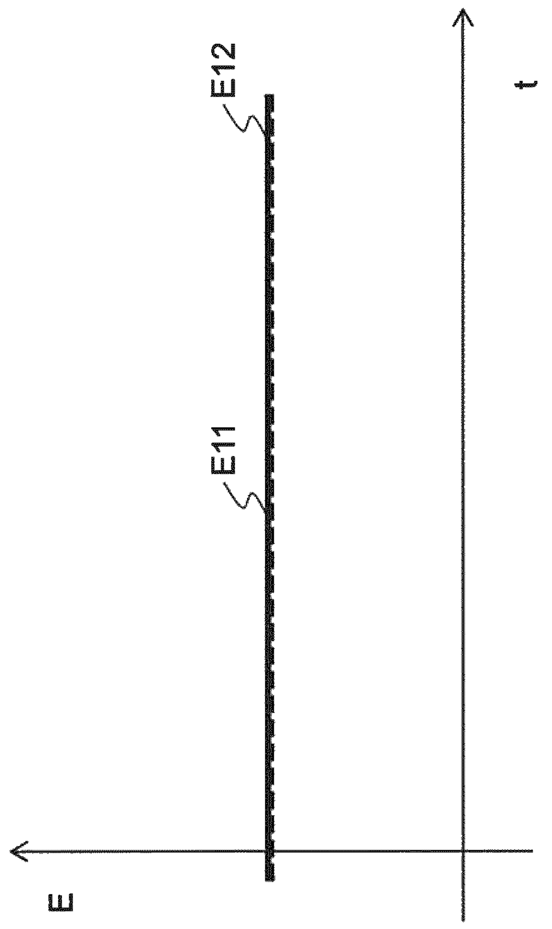
Figure 11:
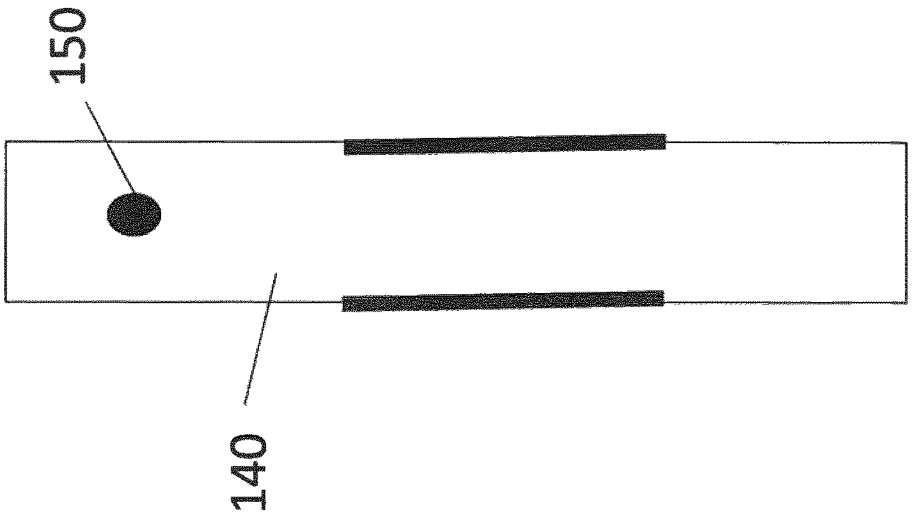
Figure 12:
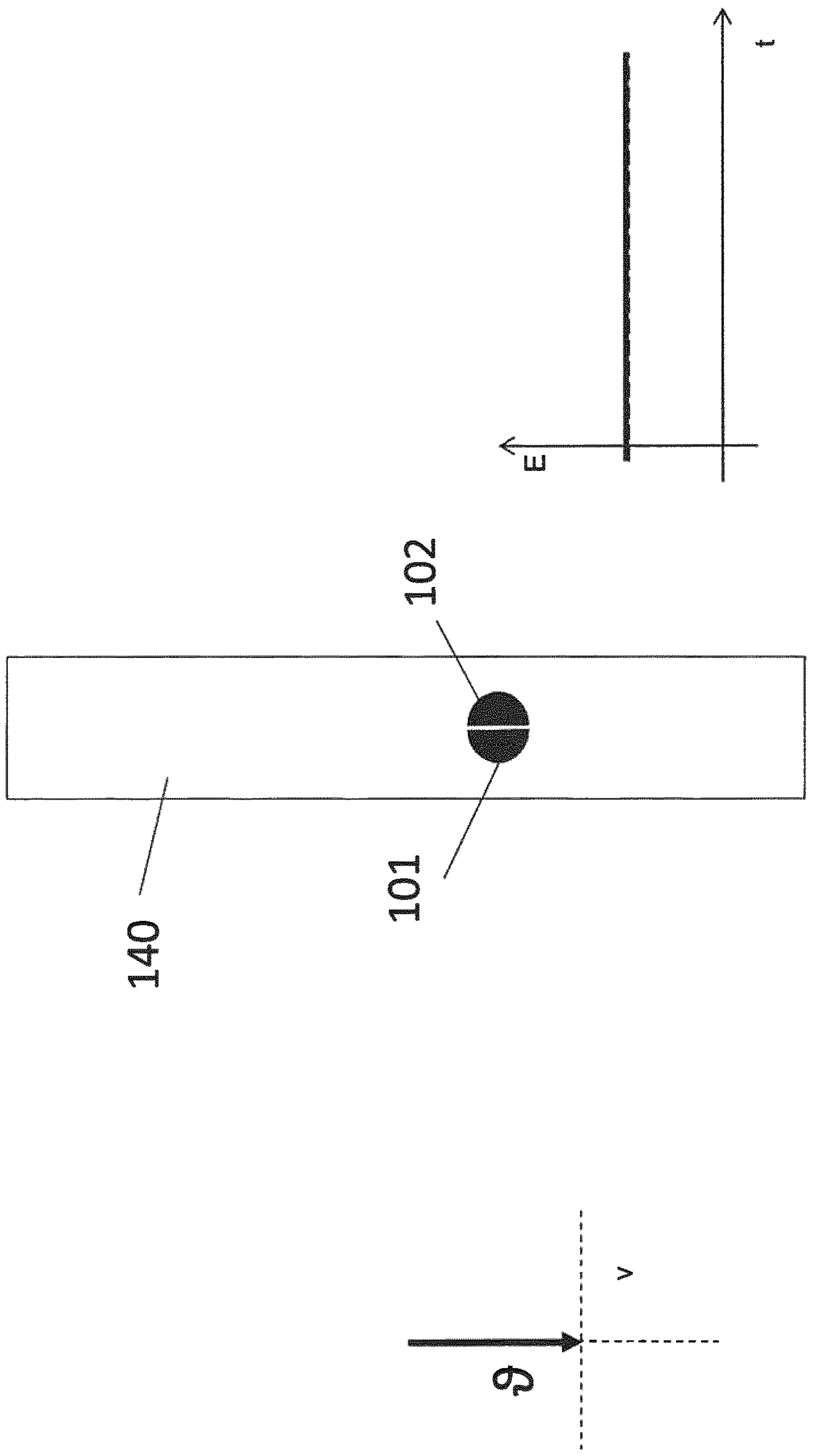
Figure 13:
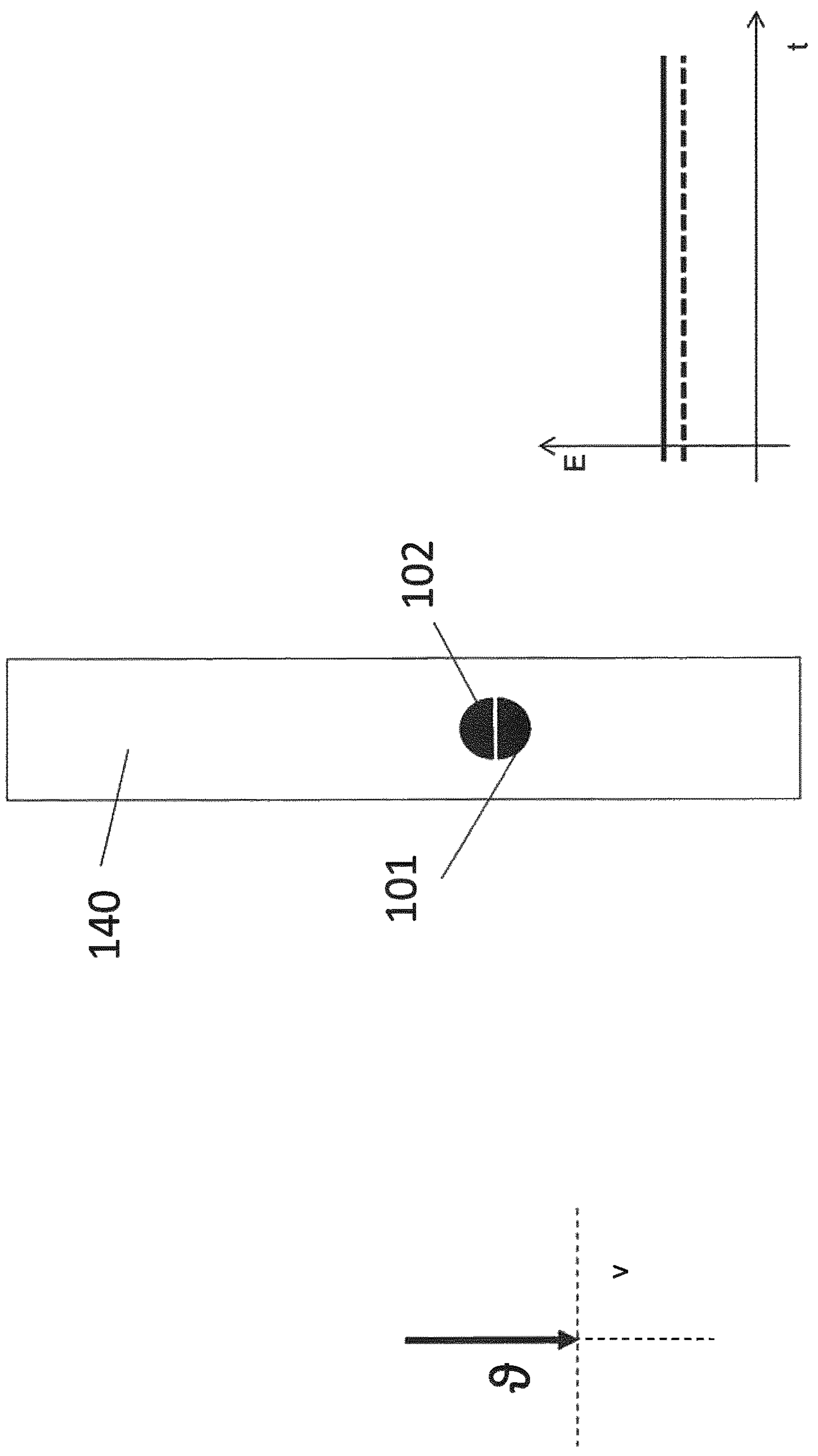

FIG. 1 schematically illustrates two sensors positioned on a catheter with the sensors oriented in a direction of the fluid flow;

FIG. 2 schematically illustrates two signals measured by the two sensors of FIG. 1, FIG. 3 schematically illustrates two sensors positioned on a catheter with the sensors not oriented in a direction of the fluid flow;

FIG. 4 schematically illustrates two signals measured by the two sensors of FIG. 3;

FIG. 5 schematically illustrates a carrier with a sensor arrangement;

FIG. 6 schematically illustrates a carrier being wrapped around a catheter;

FIG. 7 schematically illustrates two sensors positioned at opposite sides of a catheter;

FIG. 8 schematically illustrates two signals measured by the two sensors at the catheter of FIG. 7;

FIG. 9 schematically illustrates two sensors positioned at opposite sides of a catheter aligned with a fluid flow;

FIG. 10 schematically illustrates two signals measured by the two sensors at the catheter of FIG. 9;

FIG. 11 schematically illustrates two sensors positioned at opposite sides of a catheter and a catheter hole;

FIG. 12 schematically illustrates two sensors in semi-circular shape at a catheter in a first configuration; and FIG. 13 schematically illustrates two sensors in semi-circular shape at a catheter in a second configuration.

The variants of the functional and operational aspects as well as their functional and operational aspects described herein are only for a better understanding of its structure, its functions and properties; they do not limit the disclosure to the embodiments. The figures are partially schematic, said essential properties and effects are clearly shown enlarged or scaled down in part to clarify the functions, active principles, embodiments and technical characteristics. Every operation, every principle, every technical aspect and every feature that/which is disclosed in the figures or in the text is/can be combined with all claims, each feature in the text and the other figures, other modes of operation, principles, technical refinements and features that are included in this disclosure, or result from it, so that all possible combinations are assigned to the devices and methods described. They also include combinations of all individual comments in the text, that is, in each section of the description, in the claims and combinations between different variations in the text, in the claims and in the figures, and can be made to subject-matter of further claims. The claims do not limit the disclosure and therefore the possible combinations of all identified characteristics among themselves. All features disclosed are explicitly also individually and in combination with all other features disclosed herein.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B. An alternative wording for the same combinations is "at least one of A and B". The same applies for combinations of more than 2 elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

The arrangement will now be described with respect to the embodiments.

In the following, without being restricted thereto, specific details are set forth to provide a thorough understanding of the present disclosure. However, it is clear to the skilled person that the present disclosure may be used in other embodiments, which may differ from the details set out below.

FIG. 1 schematically illustrates two sensors (101, 102) positioned on a catheter 140 (not shown) with the sensors (101, 102) oriented in a direction of the fluid flow. The sensors (101, 102) may be thermal velocity flow sensors. The sensors (101, 102) may be positioned on a catheter 140. The sensors (101, 102) are aligned in parallel. Further, the sensors (101, 102) are oriented in a direction of (a velocity of) the fluid flow θ=0°. FIG. 2 schematically illustrates two signals (E11 and E12) measured by the two sensors (101, 102) of FIG. 1. The two signals (E11 and E12) are equal. (Correct) alignment of the catheter 140 with a fluid flow (for example a blood stream) can be determined by using thermal cross talk between the two sensors (101, 102). For example, when the elongated body/catheter 140 is correctly aligned with the (blood) flow velocity stream (also referred to as fluid flow), i.e. the angle between the two sensors is 0°, the two sensors (101, 102) will provide the same measurement (see FIG. 2).

More details and aspects are mentioned in connection with the embodiments described above or below. The embodiment shown in FIGS. 1 and 2 may comprise one or more optional additional features corresponding to one or more aspects mentioned in connection with the proposed concept or one or more embodiments described below (e.g. FIGS. 3-13).

FIG. 3 schematically illustrates two sensors (101, 102) positioned at a catheter 140 with the sensors (101, 102) not oriented in a direction of the fluid flow. The sensors (101, 102) at the catheter 140 are tilted together with the catheter (θ>0°) with respect to the blood flow velocity. For example, when the elongated body 140, e.g. a wire or the like, is tilted with an angle > or < than 0° (see FIG. 3), the two measurements will influence each other, i.e. one sensor 101 will exchange power with a slightly warmed up fluid and then the two measurements will be different (see FIG. 4). FIG. 4 schematically illustrates two signals measured by the two sensors (101, 102) of FIG. 3. Thereby, one sensor 101 is slightly heating the other sensor 102 causing a difference in measurement.

More details and aspects are mentioned in connection with the embodiments described above or below. The embodiment shown in FIGS. 3 and 4 may comprise one or more optional additional features corresponding to one or more aspects mentioned in connection with the proposed concept or one or more embodiments described above (e.g. FIGS. 1-2) or below (e.g. FIGS. 5-13).

FIG. 5 schematically illustrates a carrier 110 with a sensor arrangement. The sensor arrangement includes the two sensors FS1 and FS2 (101, 102) being thermal fluid flow velocity sensors. The carrier comprises contact pads 130. The contact pads include contact pads 1 to 7. Further, the sensor arrangement includes a temperature sensor TS (120). FS1 is connected to electrical contact pads 1 and 2 via printed circuit lines. FS2 is connected to electrical contact pads 3 and 4 via printed circuit lines. TS is connected to electrical contact pads 5, 6 and 7 via printed circuit lines. Specifically, FS1, FS2 and TS are aligned in a common main dimension of their sensor dimensions. The gap between FS1 and FS2 is given by a dimension d. d may be chosen such that connecting lines between contact pads and respective sensors do not touch, as seen in FIG. 5. The carrier 110 is a flat plane, when not wrapped around a catheter 140.

More details and aspects are mentioned in connection with the embodiments described above or below. The embodiment shown in FIG. 5 may comprise one or more optional additional features corresponding to one or more aspects mentioned in connection with the proposed concept or one or more embodiments described above (e.g. FIGS. 1-4) or below (e.g. FIGS. 6-13).

FIG. 6 schematically illustrates a carrier being wrapped around a catheter. On the left side of FIG. 6, the carrier 140 is flat, and on the right side, the carrier 140 is wrapped around the catheter 140. The carrier is one of the possibilities to arrange the sensors (101, 102, 120) at the catheter. For example, the two thermal sensors (101, 102) are screen printed on a polyimide foil and then wrapped around an elongated body (the catheter 140).

More details and aspects are mentioned in connection with the embodiments described above or below. The embodiment shown in FIG. 6 may comprise one or more optional additional features corresponding to one or more aspects mentioned in connection with the proposed concept or one or more embodiments described above (e.g. FIGS. 1-5) or below (e.g. FIGS. 7-13).

FIG. 7 schematically illustrates two sensors (101, 102) positioned at opposite sides of a catheter 140. One of the two sensors 101 is effected more by the fluid flow than the other sensor 102, such that the measuring results differ. (Correct) alignment of the catheter 140 with a fluid flow (for example a blood stream) can be determined by using different positioning of the sensors (101, 102) at the catheter 140. This may be done by adjusting the gap d of FIG. 5. The two sensors (101, 102) may then be exposed differently to a current (blood) fluid flow. For example, when the catheter 140 is not aligned (tilted or rotated), one sensor 101 will be better exposed to the fluid flow (for example blood stream) than the other sensor 102. This may provide an imbalance of the measurements indicating that the two sensors (101, 102) are not correctly aligned with the fluid flow (see FIG. 8). FIG. 8 schematically illustrates two signals (E11 and E12) respectively measured by the two sensors (101, 102) at the catheter 140 of FIG. 7. The difference in measurements are due to the different exposition of the two sensors (101, 102) to the blood flow.

More details and aspects are mentioned in connection with the embodiments described above or below. The embodiment shown in FIGS. 7 and 8 may comprise one or more optional additional features corresponding to one or more aspects mentioned in connection with the proposed concept or one or more embodiments described above (e.g. FIGS. 1-6) or below (e.g. FIGS. 9-13).

FIG. 9 schematically illustrates two sensors (101, 102) positioned at opposite sides of a catheter 140 aligned with a fluid flow. FIG. 10 schematically illustrates two signals (E11 and E12) measured by the two sensors (101, 102) at the catheter 140 of FIG. 9. The two signals (E11 and E12) are aligned with the fluid flow, when the catheter 140 is aligned with the fluid flow. For example, when the two sensors (101, 102) are equally aligned with the fluid flow (stream) (see FIG. 9), measurements of the two sensors (101, 102) may provide an (almost) equal signal.

More details and aspects are mentioned in connection with the embodiments described above or below. The embodiment shown in FIGS. 9 and 10 may comprise one or more optional additional features corresponding to one or more aspects mentioned in connection with the proposed concept or one or more embodiments described above (e.g. FIGS. 1-8) or below (e.g. FIG. 11-13).

One or more embodiments may comprise a catheter 140 or wire (elongated body). The catheter 140 or elongated body can have or can be equipped with a (blood) flow velocity sensor (101, 102). The (blood) flow velocity sensor (101, 102) may provide information on its own correct alignment. Thus, the (blood) flow velocity sensor (101, 102) may provide feedback of an alignment of the catheter 140. Consequently, the catheter 140 can be repositioned and the measurement can be accurately taken. The (blood) flow velocity sensor (101, 102) may be used in combination with a temperature sensor 120. The (blood) flow velocity sensor (101, 102) may be a thermal (blood) flow velocity sensor (101, 102) constituted by two sensors in parallel.

FIG. 11 schematically illustrates two sensors positioned at opposite sides of a catheter 140 and a pressure sensor 150. Thus, FIG. 11 provides an elongated body 140 with flow, temperature and pressure sensor.

FIG. 12 schematically illustrates first and second sensors 101 and 102 in semi-circular shape at a catheter in a first configuration. The first and second sensors may be flow sensors.

The first sensor 101 may have a semi-circular shape. The second sensor 102 may have a semi-circular shape. The first 101 and second 102 sensor may be in the form of a semi-circle. A flat part of the semi-circle of the first sensor 101 and a flat part of the semi-circle of the second sensor 102 may be parallel. The flat parts of the first 101 and second 102 sensors may be aligned with a direction/orientation of the catheter 140.

FIG. 13 schematically illustrates first 101 and second 102 sensors in semi-circular shape at a catheter in a second configuration. The second orientation is turned 90 degrees from the first orientation. Thus, FIG. 13 illustrates a variation of FIG. 12 with sensors rotated by 90°. The flat parts of the first 101 and second 102 sensors may be non-aligned with a direction/orientation of the catheter 140 (90 degrees turned).

The different arrangements (first and second configurations) of the first 101 and second 102 sensors at the catheter 140 may lead to different measurements of the respective first 101 and second 102 sensors. When the fluid flow is in a direction of an orientation of the catheter, the measurements of the respective first 101 and second 102 sensors may be equal in the first configuration (see FIG. 12). When the fluid flow is in a direction of an orientation of the catheter, the measurements of the respective first 101 and second 102 sensors may be different in the second configuration (see FIG. 13).

More details and aspects are mentioned in connection with the embodiments described above or below. The embodiment shown in FIGS. 11 to 13 may comprise one or more optional additional features corresponding to one or more aspects mentioned in connection with the proposed concept or one or more embodiments described above (e.g. FIGS. 1-10) or below.

In one or more embodiments, measurements of the two parallel sensors (101, 102) may be compared with an automatic system (e.g. microcontroller or CPU).

In one or more embodiments, first 101 and second 102 sensors may be displaced and parallel to each other. A shape of the first 101 sensor and a shape of the second 102 sensor may be in the form of a half circle. The first 101 and second 102 sensors may have a first dimension. The first 101 and second 102 sensors may have a second dimension. The first 101 and second 102 sensors may have a third dimension. The first dimension may be a flat part. The second dimension may be an arc. The third dimension may be a height. The total fluid's velocity may be the one measured by the sum of the first 101 and second 102 sensors. By comparing the two measurements made by the first 101 and second 102 sensors it is possible to derive a direction of the fluid flow.

The aspects and features mentioned and described together with one or more of the previously detailed examples and figures, may as well be combined with one or more of the other examples in order to replace a like feature of the other example or in order to additionally introduce the feature to the other example.

The description and drawings merely illustrate the principles of the disclosure. Furthermore, all examples recited herein are principally intended expressly to be only for pedagogical purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

The present disclosure is not limited in any way to the embodiments described above. On the contrary, there are many possibilities for modifications thereof, which are apparent to an average skilled person without departing from the underlying idea of the present disclosure as defined in the appended claims.

The invention claimed is:

1. An arrangement for providing information of an alignment of a catheter, the arrangement comprises:

a catheter;

a sensor arrangement comprising a first sensor and a second sensor, wherein the first and the second sensors are adapted to measure respective velocities of a fluid flow, and wherein the first and second sensors are each adapted to provide information such that an alignment of the catheter with respect to a direction of the fluid flow is determinable based on the respective velocities of the fluid flow measured by the first and second sensors, wherein the information is a measured signal, and the alignment is determinable by analysing a difference between the measured signals, wherein the first and second sensors are arranged at a circumference of the catheter and spaced to each other, wherein the spacing is greater than 10 μm and less than 15% of the circumference of the catheter, wherein the first and second sensors are each thermal flow velocity sensors, wherein an axis of the first sensor is parallel to an axis of the second sensor, and wherein the first and second sensors are arranged such that when the catheter is directly aligned with the fluid flow, the first and second sensors provide the same measurement, and when the catheter is not directly aligned with the fluid flow, the first and second sensors provide different measurements which include thermal cross talk between the first and second sensors.

2. The arrangement according to claim 1, wherein the sensor arrangement further comprises a third sensor and wherein the third sensor is a pressure sensor adapted to measure pressure of a fluid corresponding to the fluid flow.

3. The arrangement according to claim 1, wherein the first and second sensors are spaced from the circumference of the catheter.

4. The arrangement according to claim 1, further comprising:

a flexible carrier including the sensor arrangement, wherein the carrier is arranged along the circumference of the catheter, and wherein the flexible carrier is glued to the catheter.

5. The arrangement according to claim 4, wherein the sensor arrangement is spaced from the circumference of the catheter by at least half a height of the flexible carrier.

6. The arrangement according to claim 4, wherein the flexible carrier further includes electrical contact pads which are arranged and adapted to enable an electrical connection to the first and second sensors.

7. The arrangement according to claim 6, wherein a processing unit is electrically connectable or connected to the electrical contact pads, and wherein the electrical connection is established by bonding electrical wires connected to the processing unit to the electrical contact pads.

8. The arrangement according to claim 1, wherein the first and second sensors are arranged at the circumference of the catheter, such that a sensor area of the first sensor is not in the same plane as a sensor area of the second sensor.

9. The arrangement according to claim 1, wherein the sensor arrangement further comprises a third sensor adapted to measure a temperature of a fluid corresponding to the fluid flow.

10. An arrangement for providing information of an alignment of a catheter, the arrangement comprises:

a catheter;

a sensor arrangement comprising a first sensor and a second sensor, wherein the first and the second sensors are adapted to measure respective velocities of a fluid flow, and wherein the first and second sensors are arranged at a circumference of the catheter, such that a sensor area of the first sensor is not in the same plane as a sensor area of the second sensor;

wherein the first and second sensors are each adapted to provide information such that an alignment of the catheter with respect to a direction of the fluid flow is determinable based on the respective velocities of the fluid flow measured by the first and second sensors, wherein the information is a measured signal, and the alignment is determinable by analysing a difference between the measured signals, wherein the sensor arrangement further comprises a third sensor adapted to measure a temperature of a fluid corresponding to the fluid flow, and wherein the first, second, and third sensor are arranged at a circumference of the catheter; and a processing unit configured to process the respective velocities of the fluid flow provided by the first and second sensors, wherein the first and second sensors are arranged at the circumference of the catheter and spaced to each other, wherein the spacing is greater than 10 μm or less than 15% of the circumference of the catheter;

wherein the first and second sensors are each thermal flow velocity sensors, wherein an axis of the first sensor is parallel to an axis of the second sensor, and wherein the first and second sensors are arranged such that when the catheter is directly aligned with the fluid flow, the first and second sensors provide the same measurement, and when the catheter is not directly aligned with the fluid flow, the first and second sensors provide different measurements which include thermal cross talk between the first and second sensors.

11. An arrangement for providing information of an alignment of a catheter, the arrangement comprises:

a catheter;

a flexible carrier configured to wrap around and be glued to the catheter;

a sensor arrangement on the flexible carrier, the sensor arrangement comprising:

a first sensor;

a second sensor;

wherein the first and the second sensors are adapted to measure respective velocities of a fluid flow, and wherein the first and second sensors are arranged at a circumference of the catheter, such that a sensor area of the first sensor is not in the same plane as a sensor area of the second sensor;

wherein the first and second sensors are each adapted to provide information such that an alignment of the catheter with respect to a direction of the fluid flow is determinable based on the respective velocities of the fluid flow measured by the first and second sensors, wherein the information is a measured signal, and the alignment is determinable by analysing a difference between the measured signals; and a processing unit configured to process the respective velocities of the fluid flow provided by the first and second sensors;

wherein the first and second sensors are each thermal flow velocity sensors, wherein an axis of the first sensor is parallel to an axis of the second sensor, and wherein the first and second sensors are arranged such that when the catheter is directly aligned with the fluid flow, the first and second sensors provide the same measurement, and when the catheter is not directly aligned with the fluid flow, the first and second sensors provide different measurements which include thermal cross talk between the first and second sensors.

12. The arrangement according to claim 11, wherein the processing unit is configured to provide information to an outputting unit to indicate the alignment of the catheter with respect to the direction of the fluid flow, and a direction the catheter is to be moved within the fluid flow to provide the alignment of the catheter with respect to the direction of the fluid flow.

* * * * *